United States Patent
Williams et al.

(10) Patent No.: US 6,242,379 B1
(45) Date of Patent: *Jun. 5, 2001

(54) DEHYDROGENATION CATALYSTS

(75) Inventors: David Williams, Louisville, KY (US); Yuji Mishima, Fuchu-machi (JP); Andrzej Rokicki, Prospect, KY (US); Kazuhiko Shinyama, Fuchu-Machi (JP); Dennis J. Smith, Louisville, KY (US)

(73) Assignee: United Catalysts Inc., Louisville, KY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/053,234

(22) Filed: Apr. 1, 1998

(51) Int. Cl.⁷ .............. B01J 21/08; B01J 21/12; B01J 23/40; B01J 23/60; B01J 23/72
(52) U.S. Cl. .............. 502/300; 502/305; 502/309; 502/312; 502/314; 502/315; 502/316; 502/325; 502/326; 502/327; 502/328; 502/329; 502/331; 502/344; 502/349; 502/350; 502/237; 502/242; 502/243; 502/245; 502/247; 502/248; 502/250; 502/255
(58) Field of Search .............. 502/300, 325–329, 502/305, 309, 312, 314–316, 331–340, 344, 349, 350, 237, 242, 243, 245, 247, 248, 250, 255, 256, 257–263

(56) References Cited

U.S. PATENT DOCUMENTS

| | | |
|---|---|---|
| 2,408,140 | 9/1946 | Gutzeit . |
| 2,414,585 | 1/1947 | Eggertson et al. . |
| 2,426,829 | 9/1947 | Kearby . |
| 2,866,790 | 12/1958 | Pitzer . |
| 2,866,791 | 12/1958 | Pitzer . |
| 2,870,228 | 1/1959 | Armstrong et al. . |
| 3,084,125 | 4/1963 | Soderquist et al. . |
| 3,360,579 | 12/1967 | Hills et al. . |
| 3,364,277 | 1/1968 | Siem . |
| 3,424,808 | 1/1969 | Brewer et al. . |
| 3,437,703 * | 4/1969 | Reitmeier et al. . |
| 3,505,422 | 4/1970 | Brewer et al. . |
| 3,798,178 | 3/1974 | Soderquist . |
| 3,843,745 * | 10/1974 | Christmann et al. ............... 502/316 |
| 3,872,027 * | 3/1975 | Christmann et al. ............... 502/316 |
| 3,900,525 * | 8/1975 | Christmann et al. ............... 585/443 |
| 3,904,552 | 9/1975 | O'Hara . |
| 4,098,723 | 7/1978 | Riesser . |
| 4,134,858 | 1/1979 | Courty . |
| 4,144,197 | 3/1979 | Riesser . |
| 4,376,225 | 3/1983 | Vora . |
| 4,404,123 | 9/1983 | Chu . |
| 4,418,237 | 11/1983 | Imai . |
| 4,433,186 | 2/1984 | Chu . |
| 4,435,607 | 3/1984 | Imai . |
| 4,467,046 | 8/1984 | Smith et al. . |
| 4,496,662 | 1/1985 | Chu . |
| 4,565,898 | 1/1986 | O'Hara et al. . |
| 4,628,137 | 12/1986 | Chu . |
| 4,652,687 | 3/1987 | Imai et al. . |
| 4,684,619 * | 8/1987 | Moore ............... 502/330 |
| 4,691,071 | 9/1987 | Bricker . |
| 4,717,781 | 1/1988 | Imai et al. . |
| 4,749,674 | 6/1988 | Dejaifve et al. . |
| 4,758,543 | 7/1988 | Sherrod et al. . |
| 4,764,498 * | 8/1988 | Wissner et al. ............... 502/232 |
| 4,806,624 * | 2/1989 | Herber et al. ............... 585/444 |
| 4,827,066 * | 5/1989 | Herber et al. ............... 585/443 |
| 4,914,249 | 4/1990 | Benedict . |
| 4,975,407 * | 12/1990 | Dejaifve et al. ............... 502/330 |
| 5,017,543 * | 5/1991 | De Clippeleir et al. ............... 502/328 |
| 5,023,225 * | 6/1991 | Williams et al. ............... 502/304 |
| 5,190,906 * | 3/1993 | Murakami et al. ............... 502/304 |
| 5,510,552 | 4/1996 | Dellinger et al. . |
| 5,618,974 * | 4/1997 | Kurimoto et al. ............... 502/209 |
| 5,668,075 | 9/1997 | Milam et al. . |
| 5,689,023 | 11/1997 | Hamilton, Jr. . |
| 5,744,015 * | 4/1998 | Mazanec et al. ............... 501/136 |
| 5,830,425 | 11/1998 | Schneider et al. . |

FOREIGN PATENT DOCUMENTS

| | | |
|---|---|---|
| 1062678 | 7/1992 | (CN) . |
| 1145277 | 3/1997 | (CN) . |
| 43 03 715 | 8/1994 | (DE) . |
| WO 9618458 | 6/1996 | (EP) . |
| WO 9618593 | 6/1996 | (EP) . |
| WO 9618594 | 6/1996 | (EP) . |
| 49 03 9973 | 10/1974 | (JP) . |
| 97/18034 | 5/1997 | (WO) . |

* cited by examiner

Primary Examiner—Mark L. Bell
Assistant Examiner—Patricia L. Hailey
(74) Attorney, Agent, or Firm—Scott R. Cox

(57) ABSTRACT

A catalyst for the production of alkenylaromatics from alkylaromatics, wherein the catalyst is predominantly iron oxide, an alkali metal compound and a small amount of a source for palladium or platinum. Additional components of the catalyst may include compounds based on cerium, molybdenum, tungsten and other such promoters. Also a process for the production of alkenylaromatics from alkylaromatics using this catalyst.

46 Claims, No Drawings

DEHYDROGENATION CATALYSTS

BACKGROUND OF THE INVENTION

The field of art to which this invention pertains is dehydrogenation catalysts.

In the catalytic dehydrogenation of alkylaromatic hydrocarbons to alkenylaromatic hydrocarbons, e.g., the dehydrogenation of ethylbenzene to styrene, considerable efforts have been expended to develop catalysts which exhibit high conversion combined with high selectivity and increased stability.

Promoted iron oxide catalysts have been found to be especially useful in the dehydrogenation of alkylaromatic hydrocarbons to alkenylaromatic hydrocarbons. Typical commercial iron oxide-based dehydrogenation catalysts are generally promoted with the addition of other metal compounds, in the form of, but not limited to, oxides, hydroxides, carbonates, nitrates, etc. Often one of the promoters is an alkali metal compound with potassium being preferred. Other components may also be added to the dehydrogenation catalyst to provide further promotion, activation or stabilization. In all such dehydrogenation catalysts, minor amounts of modifiers are also typically present, such as organic burn-out agents: carbon black, graphite, methylcellulose, etc., which can beneficially effect the pore structure and/or other physical properties of the catalyst. In the discussion of the different metal groups, the reference will be based on the new IUPAC notation of the periodic table.

Typical catalysts used in dehydrogenation of saturated hydrocarbons to unsaturated hydrocarbons, as disclosed in U.S. Pat. No. 2,866,790, are iron oxide catalysts containing a small amount of chromium oxide as a stabilizer and a small amount of potassium compound as promoter. Improved catalysts according to this patent are made from iron oxide (39 to 47 weight percent), chromium oxide (1 to 10 weight percent), and potassium carbonate (51 to 59 weight percent).

Dehydrogenation catalysts having good physical strength are described in U.S. Pat. No. 2,866,791. These catalysts are made from 51 to 59 weight percent potassium fluoride, 1.0 to 10 weight percent chromium oxide with the balance being iron oxide (39 to 47 weight percent).

Catalysts designed for the dehydrogenation of alkylbenzenes, at elevated temperatures in the presence of steam, comprising iron oxide and as a promoter from about 1 to about 25 percent by weight of an alkali metal oxide, from about 1 to about 10 percent by weight of a rare earth metal oxide, and from about 0.1 to about 10 percent by weight calcium oxide, are disclosed in U.S. Pat. No. 4,749,674.

Another catalyst for the dehydrogenation of ethylbenzene to styrene disclosed in U.S. Pat. No. 5,510,552 contains at least one iron oxide, at least one bicarbonate, oxide or hydroxide of potassium and/or cesium, an oxide, carbonate, nitrate or hydroxide of cerium, a hydraulic cement, from about 0.2 to about 10 percent of a sodium oxide and from about 1.5 to about 20 percent calcium oxide.

WO 96/18458 discloses a method of preparing an iron oxide catalyst comprising contacting an iron oxide with a additive comprising an element selected from a large group of elements on the periodic chart, heating that iron oxide mixture to a temperature of at least about 600°, to afford structural rearrangement of the particle habit of said iron oxide, and then forming it into the catalyst. See also WO 96/18594 and WO 96/18593.

Similarly, U.S. Pat. No. 5,668,075 discloses the preparation of improved selectivity iron oxide dehydrogenation catalysts based on reconstructed iron oxides. The reconstruction of the oxides comprises contacting an iron oxide with a dopant substance comprising elements selected from a large group of components of the periodic chart and heating the doped iron oxide to a temperature of at least about 600° C., preferably 800° C. and 1100° C. As in the previous references, rearrangement of particle habit is induced in iron oxide prior to it being formed into catalyst. Metal additives, disclosed in the teachings of the patent, are solely and specifically used to promote the physical transformation of the iron oxide and not the chemical properties of the catalyst formed based on the oxide.

Another dehydrogenation catalyst, which contains smaller amounts of iron oxide and relatively larger amounts of cerium oxide and potassium carbonate, is disclosed in U.S. Pat. No. 4,758,543.

Catalysts having good activity and good selectivity are described in U.S. Pat. No. 3,904,552. These catalysts are made with iron oxide and alkali metal oxides plus molybdenum oxide and cerium oxide. Similar catalysts utilizing tungsten oxide in place of molybdenum oxide are described in U.S. Pat. No. 4,144,197.

Dehydrogenation catalysts which maintain high activity and selectivity over extended periods of time are described in U.S. Pat. No. 4,467,046. These catalysts contain iron oxide, an alkali metal compound, a cerium compound, a molybdenum compound and a calcium compound.

Improving stability of Fe/K/Ce/Mo/Ca/Mg oxide catalysts by incorporation of small amounts of chromium (100 to 5000 ppm) into the iron oxide prior to forming the catalyst is taught in U.S. Pat. No. 5,023,225.

The addition of titanium also results in improved activity and selectivity of iron oxide/potassium oxide catalytic systems, for ethylbenzene to styrene dehydrogenation, according to U.S. Pat. No. 5,190,906.

Dehydrogenation catalysts made from iron oxide, chromium oxide and kaolinite plus potassium oxide are disclosed in U.S. Pat. No. 4,134,858. The catalysts can also contain at least one oxide of copper, vanadium, zinc, magnesium, manganese, nickel, cobalt, bismuth, tin, or antimony.

U.S. Pat. Nos. 3,424,808 and 3,505,422 are directed to dehydrogenation catalysts which consist essentially of iron oxide, a minor amount of an alkali metal hydroxide or carbonate, and a minor amount of transition metal, preferably ruthenium, cobalt, or nickel.

Catalysts for the dehydrogenation of para-ethyltoluene to para-methylstyrene are described in U.S. Pat. Nos. 4,404,123; 4,433,186; 4,496,662; and 4,628,137. These catalysts are made with iron oxide and potassium carbonate, plus chromic oxide, gallium trioxide, or magnesium oxide. Each patent also discloses that the catalysts can optionally contain compounds of cobalt, cadmium, aluminum, nickel, cesium, and rare earth elements as stabilizers, activators and promoters. Other dehydrogenation catalysts and procedures for their use and manufacture are shown in U.S. Pat. Nos. 2,408,140; 2,414,585; 3,360,579; 3,364,277; and 4,098,723.

Dehydrogenation reactions are normally conducted at the highest practical throughput rates to obtain optimum yield. Yield is dependent upon conversion and selectivity of the catalyst.

Selectivity of the catalyst is defined as the proportion of the desired product, e.g., styrene, produced to the total amount of feedstock, e.g., ethylbenzene, converted. Activity or conversion is that portion of the feedstock which is converted to the desired product and by-products.

Improvements in either selectivity or activity can result in substantially improved operating efficiency. Higher activity catalysts, for example, would allow operation at lower temperatures than currently available catalysts, for any given conversion. Thus, in addition to high energy efficiency, the catalyst would be expected to last longer and generate less thermal by-products.

The ratio of benzene to toluene, B/T ratio, in the final product is another criteria to be used in determining effectiveness of the catalyst. The benzene by-product produced can be recycled for later processing. Toluene can not be easily recycled and is considered an undesirable by-product. Thus catalysts yielding higher B/T by-product ratio, all other factors the same, will be preferred.

There is thus a need for a dehydrogenation catalyst which has good selectivity and activity.

It is, therefore, an object of the invention to provide a novel dehydrogenation catalyst.

It is another object of the invention to provide an improved dehydrogenation catalyst having both high activity and selectivity.

It is another object of this invention to provide an improved catalyst for the conversion of ethylbenzene to styrene, with high activity and high selectivity.

It is another object of the invention to provide an improved dehydrogenation catalyst containing at least iron oxide, an alkali metal oxide, and palladium and/or platinum as a promoter.

It is still a further object of this invention to provide an improved process for the production of olefinic compounds, particularly styrene. These and other objects are obtained by the product and process of the present invention.

SUMMARY OF THE INVENTION

This invention is directed to an improved dehydrogenation catalyst, preferably for use in the dehydrogenation of ethylbenzene to styrene.

The catalyst of this invention is comprised of about 30 to about 90 weight percent of at least one iron compound, about 1 to about 50 weight percent of a compound selected from the group consisting of oxide, hydroxides, carbonates and bicarbonates of alkali metals, and about 0.1 ppm to about 5000 ppm of palladium and/or platinum, wherein said weight percents are based on the total catalyst weight. Preferably, palladium is used. In addition, preferably, the catalyst also contains one or more of the compounds selected from cerium, molybdenum or tungsten, magnesium or calcium, a Group 4 metal, preferably titanium, and chromium.

The invention is also directed to a process for the production of olefinic compounds by dehydrogenation, utilizing the above-described catalyst. The invention is preferably an improved process for the production of styrene from ethylbenzene utilizing the above-described catalyst.

DESCRIPTION OF THE INVENTION

The catalysts of this invention are made by combining an iron compound, such as iron oxide or a ferrite, preferably potassium ferrite, with an alkali metal source, which can be in the form of, but is not limited to, oxides, hydroxides, carbonates, nitrates or bicarbonates, preferably a sodium or potassium derivative, and most preferably potassium carbonate, and a source for palladium or platinum, with palladium being preferred. The source for palladium and/or platinum may include elemental platinum, elemental palladium, compounds containing palladium and/or platinum or combination thereof.

In addition to the above-described components, the catalyst preferably also includes as promoters an oxide or salt of the lanthanides having atomic number of 57 to 62, most preferably cerium. The catalyst preferably also includes molybdenum or tungsten compounds, preferably oxides, most preferably molybdenum oxide. The catalyst preferably also includes alkaline earth metal compounds, most preferably magnesium oxide or calcium oxide. The catalyst may also include a source for titanium, chromium or silicon or aluminum, preferably an oxide or salt. The catalyst may also include a source for at least one of the following elements including zinc, manganese, copper, cobalt and vanadium and combinations thereof.

In a preferred embodiment, the catalyst of this invention is composed of about 30 to about 90 weight percent iron oxide calculated as $Fe_2O_3$, about 1 to about 50 weight percent of the oxide, hydroxide, carbonate, or bicarbonate of an alkali metal, calculated as an oxide and about 0.1 ppm to about 5000 ppm of platinum and/or palladium, preferably palladium, wherein said weight percents are based on the total catalyst weight. Preferably, the catalyst also contains as promoters one or more of the following: about 0.5 to about 25 weight percent cerium oxide calculated as $CeO_2$, from about 0.5 to about 10.0 weight percent molybdenum oxide or tungsten oxide calculated as $MoO_3$ or $WO_3$, from about 0.2 to about 10.0 weight percent an alkaline earth metal oxide, preferably magnesium or calcium oxide. Additional components of the catalyst may include from about 50 ppm to about 4.0 weight percent of chromium oxide calculated as $Cr_2O_3$ and from about 10 ppm to about 2000 ppm of titanium oxide calculated as $TiO_2$. The catalyst may also include from about 0.1 to about 10.0 weight percent of the salt or oxide of one or more of the following: aluminum, silicon, zinc, manganese, cobalt, cadmium, vanadium and copper, alone or in combination, calculated on an elemental basis.

An effective dehydrogenation catalyst contains from about 40 to about 90 weight percent iron oxide calculated as $Fe_2O_3$, from about 5 to about 20 weight percent of an alkali metal compound calculated as an alkali metal oxide, from about 0.1 ppm to about 1,000 ppm of a source of palladium or platinum selected from the group including elemental palladium, elemental platinum, compounds containing palladium, compounds containing platinum and combinations thereof, from about 0.5 to about 10.0 weight percent of a molybdenum or tungsten compounds calculated as $MoO_3$ or $WO_3$, and from about 4.0 to about 12.0 weight percent of a cerium compound, calculated as $CeO_2$, wherein all weight percents are based on the total weight of the catalyst. Additional promoters may be included with this catalyst as discussed above.

A most preferable dehydrogenation catalyst contains from about 40 to about 90 percent iron oxide calculated as $Fe_2O_3$, about 5 to about 20 percent of an alkali metal compound, preferably potassium oxide, about 4.0 to about 12 percent of cerium oxide calculated as $CeO_2$, about 0.5 to about 10.0 percent of molybdenum or tungsten oxide calculated as $MoO_3$ or $WO_3$, preferably molybdenum oxide, about 0.2 to about 10.0 percent of calcium or magnesium oxide, preferably calcium oxide, about 10 ppm to about 1000 ppm of titanium oxide calculated as $TiO_2$, about 100 ppm to about 2000 ppm of chromium oxide calculated as $Cr_2O_3$, and about 1 ppm to about 1000 ppm of a source for palladium or platinum, preferably palladium, calculated on an elemental basis. Additional components that can be added to this catalyst include from about 0.1 to about 10.0 weight percent of an oxide of aluminum, silicon, manganese, copper, zinc, cadmium, vanadium, and cobalt, calculated on an elemental basis.

It is advantageous to prepare the catalyst using one or a combination of the following methods: co-precipitation, decomposition, impregnation and mechanical mixing or any other method, as would be readily appreciated by those skilled in the art. The method chosen should guarantee intimate mixing and uniform distribution of the components.

It is well established in the art that different forms of iron oxide, red, yellow, brown and black, can be used for preparation of the dehydrogenation catalyst. Likewise, it is known in the art that the iron oxides can be derived from a variety of precursor materials, both natural and synthetic, using a number of processes. Generally, iron is added to the catalyst compositions as red iron oxide, $Fe_2O_3$, or yellow iron oxide, $Fe_2O_3.H_2O$, but others can be readily utilized as would be appreciated by those skilled in the art. Particularly suited are pigment grades of the iron oxides. Ferrites may also be used, such as potassium ferrite.

Likewise, the catalyst promoter can be any material taught by the art, for example, an alkali metal compound(s). Potassium compounds are the preferred alkali metal promoters. The promoter can be added to the catalyst in various forms. Alkali metal oxides, hydroxides, carbonates, bicarbonates, and the like, and mixtures thereof are preferred, with potassium carbonate or a mixture of potassium carbonate with potassium oxide is most preferred.

The catalyst compositions of the present invention also may contain, and preferably do contain compounds of cerium to enhance conversion and/or selectivity depending on the co-promoters. Cerium, if used in the catalyst compositions of the present invention, can be added to the catalyst in the form of cerium oxide or in the form of other cerium compounds, as for example, cerium carbonate, cerium nitrate, cerium hydroxide, or any combination thereof.

Other known catalyst additives can be included in the catalysts of the present invention, but are not essential. A chromium compound, which can serve as a stabilizer for the active catalytic components, is illustrative of an optional, but preferred, additive. Chromium compounds are added to alkali-promoted iron oxide catalysts to extend their life and improve stability at low steam to oil conditions of operation. Chromium, as used in the compositions of the present invention, can be added to the catalyst in the form of a chromium oxide or in the form of a chromium salt. Preferably, chromium is added by spiking of the iron oxide used in catalyst preparation as taught in U.S. Pat. No. 5,023,225.

The addition of titanium is taught in U.S. Pat. No. 5,190,906. Other optional components, used to improve selectivity of the catalyst, include molybdenum or tungsten, which can be added as respective oxides or salts, including derivatives of corresponding oxo acids (i.e. molybdates or tungstates, respectively). In addition, a number of other metal compounds may be added as promoters. These can include, but are not limited to, compounds of aluminum, vanadium, cobalt, cadmium, copper, calcium, magnesium, and manganese.

The physical strength, activity and selectivity of the catalyst compositions of the present invention can be improved by adding certain binding agents. Binding agents can include, but are not limited to, hydraulic cements, calcium aluminate or Portland cement. These agents can be added individually or in combination.

The density of the catalyst composition can be modified by the addition of various filler substances, for example, combustible materials such as graphite and methyl cellulose. Such materials can be added to the compositions during preparation, but are burned out after the catalyst pellets have been formed during the calcining step. Porosity promoting aids can also facilitate extrusion of catalyst pellets.

The catalyst components can be mixed in various ways known to the art. One method comprises ball milling together a mixture of desired compounds, adding a small amount of water, and extruding the composite to produce small pellets, which are then dried and calcined. Another method is mixing the components together with water, drying them to form a powder, and tableting and calcining the tablets. Another procedure involves mixing the components together with an excess of water, partially drying, and then subsequently extruding, drying, and calcining the resulting pellets. The choice of the mixing method depends on the preference of the skilled artisan.

A preferred method of preparing the catalyst is to blend the catalyst ingredients together in the presence of sufficient water to make a moist extrudable mixture. This mixture is then extruded to produce extrudates of desired shape and size, typically cylindrical pellets having a diameter of about 3 mm. The extrudates are then calcined under conventional calcining conditions. Calcination temperatures can range from about 500° C. to about 1200° C., preferably from about 600° C. to about 1000° C. After calcination, the extrudates are ready for use as catalysts.

Known methods can be used to form the catalyst mass. Preferred forming methods are pelletizing, extruding and tableting, in which the use of inorganic or organic auxiliaries as lubricants to improve plasticity during extrusion is recommended. Forming can also be undertaken both before and after calcination.

The efficacy of the palladium or platinum addition is independent of the method of addition or the point in the manufacturing process at which it is incorporated. The following are some methods for delivery of the palladium or platinum promoter. A number of alternative methods would be obvious to one skilled in the art.

The palladium or platinum additives can be directly added to the iron oxide and the mixture can be pre-fired at about 300° C. to about 500° C. prior to blending with the other components. Alternatively, the palladium or platinum can be co-precipitated with iron oxide prior to the iron oxide being blended. In yet another embodiment, the palladium and platinum additives can be impregnated onto the surface of the finished catalyst followed by drying and re-calcination at a temperature adequate to drive-off water and decompose the impregnated salt. However, addition of the palladium or platinum metal additives in the form of an aqueous solution of appropriate salts, preferably nitrates, directly to the catalyst blend, immediately prior to mulling and pelletizing, is preferred.

Heat treatment or calcination can be conducted under static conditions, for example, in a tray furnace, or under dynamic conditions, such as in a rotary kiln. The temperatures and residence times are determined for each individual type of catalyst. The catalysts preferably occur as moldings, especially in the form of spheres, pellets, rings, tablets or extruded products, in which they are formed as solid or hollow objects in order to achieve a high geometric surface with a simultaneously low resistance to flow.

The BET surface area of the catalysts is typically about 0.5 to about 12 $m^2/g$, and preferably, about 1.5 to about 4 $m^2/g$. The BET surface is determined by $N_2$ adsorption, as described in ASTM D3663-92.

The specific pore volume is determined according to the mercury penetration method described in J. Van Brakel, et al., Powder Technology, 29, p.1 (1981). In this method, mercury is pressed up to a pressure of about 4000 bar into the catalyst moldings, during which the volume reduction of the mercury is plotted as a function of pressure. A curve is obtained from which the pore distribution can also be determined. According to this mercury penetration method, only the volume and distribution of pores with a diameter of >3.6 nm can be determined. Generally, catalysts with larger pore volume and higher median pore diameter are preferred as taught in U.S. Pat. No. 5,689,023. Typical pore volume of the catalysts of the present invention is in the range of ca. 0.10 to 0.45 cc/g.

One skilled in the art will readily appreciate that surface area, total pore volume and pore volume distribution can be adjusted with proper manufacturing techniques to get optimum performance for any given catalyst composition. This not withstanding, the promotional effect of palladium or platinum addition to the formulations will still be unmistakable.

The catalysts of the present invention are effective as dehydrogenation catalysts and especially effective in promoting the dehydrogenation of ethylbenzene to produce styrene. Such dehydrogenation reactions are generally carried out at reaction temperatures from about 480° C. to about 700° C., preferably about 535° C. to about 650° C. The use of subatmospheric, atmospheric, or super atmospheric pressures are suitable for the reactions. However, based on equilibrium and selectivity considerations, it is preferred to operate at as low a pressure as is feasible. Therefore, atmospheric or subatmospheric pressure is preferred. Typically the dehydrogenation process using the catalysts of this invention is conducted as a continuous operation utilizing a fixed bed which may consist of a single stage or a series of stages of the same or different catalysts in one or more reactors. Other types of reactors and reactor configurations can be used for the dehydrogenation process.

In the dehydrogenation process using the catalyst of this invention, steam is added to the hydrocarbon feedstock to aid in the removal of carbonaceous residues from the catalyst and to furnish heat for the reaction. Steam to hydrocarbon molar ratios from about 3 to about 18 or higher can be used. However, in order to conserve energy in the operation of the process, steam to hydrocarbon molar ratios (S/O) of 12 or lower are preferred.

The contact time of the reactant-containing gas with the catalyst is expressed in terms of liquid-hourly-space velocity (LHSV) which is defined as the volume of liquid hydrocarbon reactant per volume of catalyst per hour. The LHSV of the organic reactants can vary between about 0.1 hour$^{-1}$ and about 5 hour$^{-1}$.

When used in the continuous process of dehydrogenating ethyl benzene to styrene, the catalysts of this invention exhibit better performance, i.e. higher conversion, improved yield and higher B/T ratio, than similar catalysts which do not contain palladium or platinum.

EXAMPLES

The following examples describe the invention in more detail. Parts and percentages are by weight unless otherwise designated. Iron oxide used in all the following preparations is a commercial product that may contain ppm levels of Ti and Cr and may also contain minor amounts of other elements such as Si, Al, Mn, Mg, S, Cl, Zn, V, Cu, etc.

Comparative Example 1

Comparative dehydrogenation catalyst 1, with a composition of 11.2% potassium oxide ($K_2O$), 88.8% iron oxide ($Fe_2O_3$) was prepared as follows:

A mixture of the required amounts of potassium carbonate and unhydrated iron oxide were dry blended with a small amount of organic lubricant/poreformer, mixed with water to form an extrudable paste and then formed into cylindrical pellets of 3 mm diameter. The pellets were dried several hours and then calcined (at 600° C.).

Example 2

The catalyst of Example 2 was prepared according to the procedure of Comparative Example 1, except that a palladium nitrate solution sufficient to produce a concentration of 0.072% Pd in the final catalyst was added to the water used to prepare the extrudable paste.

The catalysts of Comparative Example 1 and Example 2 were tested for ethylbenzene dehydrogenation performance in an externally heated tubular reactor of 1" internal diameter. A vaporized, preheated mixture of steam and ethylbenzene (with a molar ratio of about 12/1) was introduced to the catalyst at controlled throughput and pressure (LHSV=1 and pressure=1 atm.) over a range of temperature from 540° C. to 570° C. Dehydrogenated product exiting the reactor was collected and analyzed to determine conversion (%C) of ethylbenzene and selectivity (%S) to styrene. Table I shows the effect on performance of the catalyst prepared according to the invention.

TABLE I

| Catalyst | Comparative Example 1 | | Example 2 | |
|---|---|---|---|---|
| Palladium concentration wt. % | — | | 0.072 | |
| Dehydrogenation Performance | % C | % S | % C | % S |
| 570° C. | 46.86 | 94.62 | 50.10 | 94.27 |
| 540° C. | 25.62 | 96.15 | 33.30 | 96.04 |

Comparative Example 3

The dehydrogenation catalyst of Comparative Example 3 having the following nominal composition on oxide basis:

9.89% $K_2O$ 9.97% $CeO_2$ 2.53% $MoO_3$ 77.61% $Fe_2O_3$ was prepared as follows:

A mixture of the required amounts of potassium carbonate, cerium carbonate, molybdenum oxide, and unhydrated iron oxide were dry blended with a small amount of organic lubricant/poreformer, mixed with water to form an extrudable paste, and then formed into cylindrical pellets of 3 mm diameter. The pellets were dried several hours and then calcined at 900° C.

Examples 4 and 5

The catalysts of Examples 4 and 5 were prepared according to the procedure for the catalyst of Comparative Example 3 except that palladium nitrate solution, Example 4, or dinitrodiamine platinum solution, Example 5, sufficient to produce a concentration of 200 ppm palladium or 368 ppm platinum in the respective calcined catalysts, was added to the water used to prepare the extrudable paste for pelletizing the catalysts.

The catalysts of Comparative Example 3 and Examples 4 and 5 were granulated (to a size of 0.85 to 1.18 mm) and evaluated for ethylbenzene dehydrogenation performance in a differential type reactor (steam/oil=12 molar, p=1 atm., catalyst weight/feed rate=14.7 times (g. cat.×hr.÷mol). Dehydrogenation performance data are shown in Table II along with the indicated concentration of Pd or Pt. As in Comparative Example 1, catalyst performance was determined by analysis of the dehydrogenated product exiting the reactor.

TABLE II

| Promoter<br>Promoter Concentration wt. % | | Comparative<br>Example 3<br>none<br>— | | Example 4<br>Pd<br>0.0200 | | Example 5<br>pt<br>0.0368 | |
|---|---|---|---|---|---|---|---|
| D.P.* | | % C | % S | % C | % S | % C | % S |
| 600° C. | | 30.73 | 98.41 | 35.94 | 98.21 | 35.54 | 98.51 |
| 585° C. | | 21.60 | 98.77 | 28.56 | 98.63 | 27.59 | 98.90 |
| 570° C. | | 14.23 | 98.96 | 21.94 | 98.89 | 21.41 | 99.13 |
| 555° C. | | 9.15 | 99.09 | 16.32 | 99.08 | 16.15 | 99.25 |
| 540° C. | | 5.54 | 99.13 | 11.72 | 99.20 | 12.16 | 99.32 |

*Dehydrogenation Performance

TABLE III

| Promoter<br>Promoter Concentration wt. % | | Comparative<br>Example 6<br>none<br>— | | Example 7<br>Pd<br>0.0200 | | Example 8<br>pt<br>0.0368 | |
|---|---|---|---|---|---|---|---|
| D.P.* | | % C | % S | % C | % S | % C | % S |
| 600° C. | | 30.18 | 98.55 | 43.04 | 97.87 | 37.12 | 98.58 |
| 585° C. | | 21.10 | 98.89 | 34.60 | 98.43 | 28.79 | 98.95 |
| 570° C. | | 14.39 | 99.05 | 27.06 | 98.82 | 22.16 | 99.15 |
| 555° C. | | 9.49 | 99.15 | 20.65 | 99.00 | 16.78 | 99.28 |
| 540° C. | | 5.91 | 99.19 | 14.99 | 99.17 | 12.74 | 99.37 |

*Dehydrogenation Performance

Comparative Example 6

The dehydrogenation catalyst of Comparative Example 6 having the following nominal composition, on oxide basis:

9.89% $K_2O$ 9.97% $CeO_2$ 2.53% $WO_3$ 77.61% $Fe_2O_3$ was prepared as follows:

A mixture of the required amounts of potassium carbonate, cerium carbonate, tungsten oxide, and unhydrated iron oxide were dry blended with a small amount of organic lubricant/poreformer, mixed with water to form an extrudable paste, and then formed into cylindrical pellets of 3 mm diameter. The pellets were dried several hours and then calcined at 900° C.

Examples 7 and 8

The catalysts of Examples 7 and 8 were prepared according to the procedure for the catalyst of Comparative Example 6 except that palladium nitrate solution, Example 7, or dinitrodiamine platinum solution, Example 8, sufficient to produce a concentration of 200 ppm palladium or 368 ppm platinum in the respective calcined catalysts, was added to the water used to prepare the extrudable paste for pelletizing the catalysts.

The catalysts of Comparative Example 6 and Examples 7 and 8 were granulated (to a size of 0.85 to 1.18 mm) and evaluated for ethylbenzene dehydrogenation performance in the manner described in Example 3. Dehydrogenation performance data are shown in Table III along with the indicated concentration of Pd or Pt.

Comparative Example 9

The dehydrogenation catalyst of Comparative Example 9 having the following nominal composition, on oxide basis:

9.5% $K_2O$ 2.2% MgO 5.0% $CeO_2$ 2.5% $MoO_3$ 2.0% CaO 78.8% $Fe_2O_3$ was prepared as follows:

A mixture of the required amounts of potassium carbonate, magnesium carbonate, cerium carbonate, molybdenum oxide, calcium hydroxide and unhydrated iron oxide were dry blended with a small amount of organic lubricant/poreformer, mixed with water to form an extrudable paste, and then formed into cylindrical pellets of 3 mm diameter. The pellets were dried several hours and then calcined (at 600° C.).

Examples 10,11,12,13

The catalysts of Examples 10, 11, 12 and 13 were prepared according to the procedure for the catalyst of Comparative Example 9 except that amounts of a palladium nitrate solution, sufficient to produce the target concentration of palladium in the calcined catalyst, were added to the water used to prepare the extrudable paste for pelletizing.

The catalysts of Comparative Example 9 and Examples 10 through 13 were granulated (to a size of 0.85 to 1.18 mm) and evaluated for ethylbenzene dehydrogenation performance in the manner described in Example 3. Dehydrogenation performance data are shown in Table IV along with the indicated concentration of Pd.

TABLE IV

| Palladium Concentration wt. % | Comparative Example 9 — | | Example 10 0.12 | | Example 11 0.064 | | Example 12 0.031 | | Example 13 0.010 | |
|---|---|---|---|---|---|---|---|---|---|---|
| D.P.* | % C | % S | % C | % S | % C | % S | % C | % S | % C | % S |
| 600° C. | 34.8 | 98.4 | 44.5 | 98.0 | 43.1 | 97.8 | 40.8 | 97.9 | 47.7 | 97.3 |
| 585° C. | 24.1 | 98.9 | 36.4 | 98.5 | 34.7 | 98.3 | 33.0 | 98.3 | 39.2 | 98.1 |
| 570° C. | 16.2 | 99.1 | 28.6 | 98.7 | 26.6 | 98.4 | 25.7 | 98.5 | 30.9 | 98.6 |
| 555° C. | 10.3 | 99.1 | 21.4 | 98.9 | 19.4 | 98.5 | i9.0 | 98.8 | 23.5 | 98.9 |
| 540° C. | 6.4 | 99.1 | 15.8 | 98.9 | 13.5 | 98.S | 13.S | 98.9 | 17.0 | 99.2 |

*Dehydrogenation Performance

Comparative Example 14

The dehydrogenation catalyst of Comparative Example 14 having the following nominal composition, on oxide basis:

9.4% $K_2O$ 2.2% MgO 9.9% $CeO_2$ 2.5% $MoO_3$ 1.9% CaO 74.1% $Fe_2O_3$ was prepared as follows:

A mixture of the required amounts of potassium carbonate, magnesium carbonate, cerium carbonate, molybdenum oxide, calcium hydroxide and unhydrated iron oxide was dry blended with a small amount of organic lubricant/poreformer. Water was mulled into the mixture to form an extrudable paste. The paste was formed into cylindrical pellets of 3 mm diameter. The pellets were dried several hours and then calcined at ca. 840° C.

Examples 15, 16, 17, 18

The catalysts of Examples 15 through 18 were prepared in the manner of the catalyst of Comparative Example 14 except that amounts of a palladium nitrate solution sufficient to produce the target concentrations of Pd, in the calcined catalyst, were added to the water used to prepare the extrudable paste for pelletizing each example catalyst.

The catalysts of Comparative Example 14 and Examples 15 through 18 were tested for dehydrogenation performance in the manner described in Example 3 except that the range of temperature was 538–593° C. Dehydrogenation performance data are shown in Table V along with the indicated concentration of Pd. Δ%C is the absolute deviation in % ethylbenzene conversion of the invention example catalysts versus that of the comparative example catalyst. $\Delta\%S_{60}$ is the absolute deviation in styrene selectivity at 60% ethylbenzene conversion of the invention example catalysts versus that of the comparative example catalyst. Benzene to toluene, B/T, is the weight ratio of benzene to toluene in the products.

TABLE V

| Catalyst Pd con., wt. % | Com. Ex 14 — | | Example 15 0.0023 | | Example 16 0.0050 | | Example 17 0.020 | | Example 18 0.064 | |
|---|---|---|---|---|---|---|---|---|---|---|
| D.P*. at Temp. ° C. | Δ % C | B/T | Δ % C | B/T | Δ % C | B/T | Δ % C | B/T | Δ % C | B/T |
| 593 | 0 | .29 | 2.0 | .30 | 1.6 | .30 | 0.9 | .30 | 2.5 | .32 |
| 565 | 0 | .34 | 4.4 | .37 | 4.0 | .36 | 3.9 | .37 | 4.7 | .40 |
| 538 | 0 | .50 | 7.6 | .55 | 6.8 | .50 | 6.3 | .56 | 6.5 | .57 |
| $\Delta S_{60}$ | 0 | | −0.2 | | 0.1 | | −0.2 | | −0.2 | |

*Dehydrogenation Performance

Comparative Example 19

The dehydrogenation catalyst of Comparative Example 19 having the following nominal composition, on oxide basis:

9.5% $K_2O$ 2.2% MgO 5.0% $CeO_2$ 2.5% $MoO_3$ 2.0% CaO 78.8% $Fe_2O_3$ was prepared as follows:

A mixture of the required amounts of potassium carbonate, magnesium carbonate, molybdenum oxide, calcium hydroxide and unhydrated iron oxide were dry blended with a small amount of organic lubricant/poreformer. The required amount of an aqueous solution of cerium nitrate was mulled into the dry mixture to form an extrudable paste. The paste was formed into cylindrical pellets of 3 mm diameter. The pellets were dried several hours and then calcined (at 600° C.).

Examples 20 and 21

The catalysts of Examples 20 and 21 were prepared according to the procedure for the catalyst of Comparative Example 19 except palladium nitrate solution, Example 20, or dinitrodiamine platinum solution, Example 21, sufficient to produce a concentration of 640 ppm palladium or 1170 ppm platinum in the respective calcined catalysts, was added to the water used to prepare the extrudable paste for pelletizing the catalysts.

The catalysts of Comparative Example 19 and Examples 20 and 21 were tested in the manner described in Comparative Example 1. Dehydrogenation performance data are shown in Table VI along with the indicated concentration of Pd or Pt in the example catalysts.

TABLE VI

| Catalyst | Com. Ex 1 | Example 20 | Example 21 |
|---|---|---|---|
| Promoter | none | Pd | Pt |
| Promoter Concentration, wt. % | — | 0.064 | 0.117 |
| D.P*. at Temp. ° C. | Δ % C | Δ % C | Δ % C |
| 600 | 0 | 0.1 | 0.5 |
| 570 | 0 | 5.3 | 4.1 |
| 540 | 0 | 9.5 | 7.3 |
| Δ % $S_{60}$ | 0 | 0.14 | 0.0 |

Comparative Example 22

The dehydrogenation catalyst of comparative Example 22 having the following nominal composition, on oxide basis:
9.2% K2O
2.1% MgO
9.7% CeO2
3.9% WO3
1.9% CaO
73.2% Fe2O3
was prepared as follows:

A mixture of the required amounts of potassium carbonate, magnesium carbonate, ammonium metatungstate, calcium hydroxide and unhydrated iron oxide were blended together with enough water to form an extrudable paste. The paste was formed into cylindrical pellets of 3 mm diameter. The pellets were dried several hours and then calcined at about 840° C.

Example 23

The catalyst of Example 23 was prepared as follows. A portion of the catalyst prepared as Comparative Example 22 was post impregnated with palladium nitrate, to a level of 0.02% Pd, using standard incipient wetness techniques.

The catalysts of Comparative Example 22 and Example 23 were tested in the manner described in Comparative Example 14. Dehydrogenation performance data are shown in Table VII.

TABLE VII

| Catalyst | Com. Ex 22 | | Example 23 | |
|---|---|---|---|---|
| Pd Concentration, wt. % | — | | 0.02 | |
| D.P*. at Temp. ° C. | Δ% C | B/T | Δ% C | B/T |
| 593 | 0 | .16 | 1.6 | .23 |
| 565 | 0 | .16 | 4.7 | .27 |
| 538 | 0 | N/A | 7.0 | .42 |
| $\Delta S_{60}$ | 0 | | −0.05 | |

*D.P. = Dehydrogenation Performance

Comparative Example 24

Comparative dehydrogenation catalyst having the following nominal composition, on oxide basis:
9.0% K2O
2.1% MgO
9.5% CeO2
2.4% MoO3
2.1% CaO
74.8% Fe2O3
was prepared as follows:

A mixture of the required amounts of potassium carbonate, magnesium carbonate, cerium carbonate, molybdenum oxide, calcium hydroxide and unhydrated iron oxide were dry blended with a small amount of organic lubricant/poreformer, mixed with water to form an extrudable paste and then formed into "ribbed" extrusions with a diameter of 2.8 mm (as described in U.S. Pat. No. 5,097,091). The pellets were dried several hours and then calcined (at ~840° C.).

Example 25

The catalyst of Example 25 was prepared as follows. A portion of the catalyst prepared as Comparative Example 24 was post-impregnated with palladium nitrate, to a level of 50 ppm Pd, using standard incipient wetness techniques.

The catalysts of Comparative Example 24 and Example 25 were tested in the manner described in Comparative Example 14. Dehydrogenation performance data are shown in Table VIII.

TABLE VIII

| Catalyst | Com. Example 24 | | Example 25 | |
|---|---|---|---|---|
| Pd concentration wt. % | — | | 0.005 | |
| D.P.* at Temp ° C. | Δ% C | B/T | Δ% C | B/T |
| 593 | 0 | 0.26 | 2.5 | 0.31 |
| 565 | 0 | 0.31 | 4.5 | 0.36 |
| 538 | 0 | 0.40 | 8.7 | 0.50 |
| ΔS60 | 0 | | −0.17 | |

*D.P. = Dehydrogenation Performance

The catalysts of the present invention display improved activity, when compared to its unpromoted counterparts, as evidenced by increased conversion at otherwise identical conditions. The improved conversion is achieved at no substantial loss in selectivity. Moreover, the by-products formed with palladium or platinum promoted catalysts, of this application, have higher benzene to toluene, B/T, ratio than by-products formed with the non-promoted catalysts, Examples 2, 13 through 18, 20, 21, 23 and 25 vs. comparative Examples 1, 17, 19, 22 and 24, respectively.

Higher activity of the promoted catalysts is evident across the temperature range of the process, as demonstrated by the results of differential tests, Examples 4 and 5, 7 and 8, and 10 through 13 versus Comparative Examples 3, 6 and 9 respectively. By definition the conversions achieved in this type of testing are lower than typical for commercial operation. The advantage of the differential, micro-reactor tests is that it probes the catalyst performance in kinetic regime, free of diffusion interference, thus providing better, fundamental, insight into promoter effects. On the other hand, whole particle, integral, isothermal reactor tests, such as Examples 14 on, reflect better the expected commercial operation of the catalyst. The isothermal tests indicate that the activity increase in promoted catalysts is highest at the lower range of typical operating temperatures in the ethylbenzene to styrene dehydrogenation, Examples 10 through 22. However, this is probably due to diffusional limitations of 3.00 mm pellets and not to lack of promoter effect. Analogous results, of integral tests on smaller size, shorter diffusion path, 2.8 mm ribbed extrusions styrene catalyst demonstrate this point. Higher activity, as evidenced by increased conversion, is observed for Pd-promoted 2.8 mm ribbed extrusions as compared to unpromoted version of the catalyst, Example 25 and Comparative Example 24, respectively. The effect is evident across the temperature range, up to 621° C. Notwithstanding, increased low temperature conversion of Pd promoted 3.00 mm pellets is especially beneficial in an adiabatic system that by default has part of the bed operating at the lower end of the process temperature spectrum. The low temperature operation, for any given set conversion, in addition, brings about extended catalyst life and reduces fouling in the process as compared to the unpromoted catalyst. Advantages resulting from increased conversion of only a few tenths of a percent, not to mention on the order of several percentage points as demonstrated in this invention, are extremely significant in commercial process which may produce many millions of pounds of product per day.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A non-oxidative dehydrogenation catalyst for dehydrogenating a hydrocarbon feed stream in a dehydrogenation reactor, wherein components of the stream within the reactor comprise an alkylaromatic hydrocarbon and steam, and wherein the catalyst comprises about 30 to about 90 weight percent of an iron compound calculated as $Fe_2O_3$, about 1 to about 50 weight percent of an alkali metal source calculated as an alkali metal oxide, about 0.1 ppm to about 5000 ppm of at least one of a palladium or platinum source selected from the group consisting of elemental palladium, elemental platinum, compounds containing palladium, compounds containing platinum and combinations thereof, wherein all weight percents are based on the total weight of the catalyst.

2. The dehydrogenation catalyst of claim 1 wherein the iron compound is iron oxide.

3. The dehydrogenation catalyst of claim 1 wherein the iron compound is a potassium ferrite.

4. The catalyst of claim 1 wherein the alkali metal source is a sodium or potassium compound.

5. The dehydrogenation catalyst of claim 1 wherein the alkali metal source is selected from the group consisting of an alkali metal oxide, nitrate, hydroxide, carbonate, bicarbonate, and combinations thereof.

6. The catalyst of claim 1 wherein the alkali metal source is potassium carbonate.

7. The catalyst of claim 1 wherein the palladium or platinum source is selected from the group consisting of elemental palladium, compounds containing palladium and combinations thereof.

8. The catalyst of claim 1 wherein the palladium or platinum source is selected from the group consisting of elemental platinum, compounds containing platinum and combinations thereof.

9. The catalyst of claim 1 further comprising from about 0.5 to about 25.0 weight percent of a cerium compound calculated as $CeO_2$.

10. The catalyst of claim 1 further comprising from about 50 ppm to about 4.0 weight percent of a chromium compound, calculated as $Cr_2O_3$.

11. The catalyst of claim 1 further comprising from about 0.5 to about 25.0 weight percent of a cerium compound calculated as $CeO_2$ and from about 0.5 to about 10.0 weight percent of a molybdenum or tungsten compound calculated as $MoO_3$ or $WO_3$.

12. The catalyst of claim 1 further comprising from about 0.5 to about 25.0 weight percent of a cerium compound, calculated as $CeO_2$, from about 0.5 to about 10.0 weight percent of a molybdenum or tungsten compound calculated as $MoO_3$ or $WO_3$, and from about 0.2 to about 10.0 weight percent of a calcium or magnesium compound, calculated as an oxide.

13. The catalyst of claim 11 further comprising from about 50 ppm to about 4.0 weight percent of a chromium compound, calculated as $Cr_2O_3$.

14. The catalyst of claim 12 further comprising from about 50 ppm to about 4.0 weight percent of a chromium compound, calculated as $Cr_2O_3$.

15. The catalyst of claim 1 further comprising from about 0.5 to about 25.0 weight percent of a cerium compound calculated as $CeO_2$, from about 0.5 to about 10.0 weight percent of a molybdenum or tungsten compound calculated as $MoO_3$ or $WO_3$, from about 0.2 to about 10.0 weight percent of a magnesium or calcium compound, and from about 10 ppm to about 2000 ppm of a source for titanium calculated as $TiO_2$, all weight percents calculated as oxides.

16. The catalyst of claim 15 further comprising from about 50 ppm to about 4.0 weight percent of a chromium compound, calculated as $Cr_2O_3$.

17. The catalyst of claim 11 further comprising from about 10 ppm to about 2000 ppm of a source for titanium, calculated as $TiO_2$.

18. The catalyst of claim 17 further comprising from about 50 ppm to about 4.0 weight percent of a chromium compound calculated as $Cr_2O_3$.

19. The catalyst of claim 1 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

20. The catalyst of claim 9 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

21. The catalyst of claim 10 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

22. The catalyst of claim 11 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

23. The catalyst of claim 12 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

24. The catalyst of claim 13 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

25. The catalyst of claim 14 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

26. The catalyst of claim 15 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

27. The catalyst of claim 16 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

28. The catalyst of claim 17 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

29. The catalyst of claim 18 further comprising from about 0.1 weight percent to about 10.0 weight percent of a source for at least one of the following elements selected from the group consisting of aluminum, silicon, zinc, manganese, cobalt, copper, vanadium and combinations thereof, all weight percents calculated on an elemental basis.

30. A non-oxidative dehydrogenation catalyst for dehydrogenating a hydrocarbon feed stream in a dehydrogenation reactor, wherein components of the reaction stream within the reactor comprise an alkylaromatic hydrocarbon and steam, and wherein the catalyst comprises from about 40 to about 90 weight percent iron oxide calculated as $Fe_2O_3$, from about 5 to about 20 weight percent of an alkali metal compound calculated as an alkali metal oxide, from about 1 ppm to about 1000 ppm of a source of palladium or platinum selected from the group consisting of elemental palladium, elemental platinum, compounds containing palladium, compounds containing platinum and combinations thereof, from about 0.5 to about 10.0 weight percent of a molybdenum or tungsten compound, calculated as $MoO_3$ or $WO_3$ and from about 4.0 to about 12.0 weight percent of a cerium compound, calculated as $CeO_2$, wherein all weight percents are based on the total weight of the catalyst.

31. The catalyst of claim 30 wherein the alkali metal compound is a sodium or potassium compound.

32. The catalyst of claim 30 wherein the palladium or platinum source is selected from the group consisting of elemental palladium, compounds containing palladium and combinations thereof.

33. The catalyst of claim 30 further comprising from about 100 ppm to about 2000 ppm of a chromium compound.

34. The catalyst of claim 30 further comprising from about 0.2 to about 10.0 weight percent of a calcium or magnesium compound, calculated as an oxide.

35. The catalyst of claim 30 further comprising from about 10 ppm to about 1000 ppm of a source for titanium, calculated as $TiO_2$.

36. The catalyst of claim 33 further comprising from about 10 ppm to about 1000 ppm of a source for titanium, calculated as $TiO_2$.

37. The catalyst of claim 34 further comprising from about 100 ppm to about 1200 ppm of a chromium compound, calculated as $Cr_2O_3$ and from about 10 ppm to about 1000 ppm of a source for titanium, calculated as $TiO_2$.

38. The catalyst of claim 30 further comprising less than about 10.0 weight percent of a source for at least one of the following elements selected from the group consisting of aluminum, silicon, zinc, manganese, cobalt, copper, vanadium, and combinations thereof, all weight percents calculated on an elemental basis.

39. The catalyst of claim 33 further comprising less than about 10.0 weight percent of a source for at least one of the following elements selected from the group consisting of aluminum, silicon, zinc, manganese, cobalt, copper, vanadium, and combinations thereof, all weight percents calculated on an elemental basis.

40. The catalyst of claim 34 further comprising less than about 10.0 weight percent of a source for at least one of the following elements selected from the group consisting of aluminum, silicon, zinc, manganese, cobalt, copper, vanadium, and combinations thereof, all weight percents calculated on an elemental basis.

41. The catalyst of claim 35 further comprising less than about 10.0 weight percent of a source for at least one of the following elements selected from the group consisting of aluminum, silicon, zinc, manganese, cobalt, copper, vanadium, and combinations thereof, all weight percents calculated on an elemental basis.

42. The catalyst of claim 36 further comprising less than about 10.0 weight percent of a source for at least one of the following elements selected from the group consisting of aluminum, silicon, zinc, manganese, cobalt, copper, vanadium, and combinations thereof, all weight percents calculated on an elemental basis.

43. The catalyst of claim 37 further comprising from about 0.1 to about 10.0 weight percent of a source for at least one of the following elements selected from the group consisting of aluminum, silicon, zinc, manganese, cobalt, copper, vanadium, and combinations thereof, all weight percents calculated on an elemental basis.

44. A non-oxidative dehydrogenation catalyst for dehydrogenating a hydrocarbon feed stream in a dehydrogenation reactor, wherein components of the stream within the reactor comprise an alkylaromatic hydrocarbon and steam, and wherein the catalyst comprises from about 40 to about 90 weight percent iron oxide calculated as $Fe_2O_3$, from about 5 to about 20 percent of a potassium compound calculated as potassium oxide, from about 1.0 ppm to about 1000 ppm of a source for platinum or palladium selected from the group consisting of elemental platinum, elemental palladium, compounds containing platinum, compounds containing palladium and combinations thereof, from about 0.5 to about 10.0 weight percent of a molybdenum or tungsten compound calculated as $MoO_3$ or $WO_3$, from about 4.0 to about 12.0 weight percent of a cerium compound calculated as $CeO_2$, from about 0.2 to about 10.0 weight percent of a calcium or magnesium compound calculated as an oxide, from about 100 ppm to about 2000 ppm of a chromium compound calculated as $Cr_2O_3$, and from about 10 ppm to about 1000 ppm of a source for titanium calculated as $TiO_2$, wherein all weight percents are based on the total weight of the catalyst.

45. The catalyst of claim 44 wherein the source for platinum or palladium is selected from the group consisting of elemental palladium, compounds containing palladium and combinations thereof.

46. The catalyst of claim 44 further comprising from about 0.1 weight percent to about 10.0 weight percent of a source for at least one of the following elements selected from the group consisting of aluminum, silicon, manganese, cobalt, copper, vanadium, and combinations thereof, calculated on an elemental basis.

* * * * *

UNITED STATES PATENT AND TRADEMARK OFFICE
CERTIFICATE OF CORRECTION

PATENT NO. : 6,242,379 B1
DATED : June 5, 2001
INVENTOR(S) : David Williams; Yuji Mishima; Andrzej Rokicki; Kazuhiko Shinyama; Dennis J. Smith It is certified that error appears in the above-identified patent and that said Letters Patent is hereby corrected as shown below:

Title page,
Assignee should read as follows:
[73] Assignees: United Catalysts, Inc., Louisville, KY (US); Nissan Girdler Catalysts Co., Ltd. (JP)

Signed and Sealed this

Twentieth Day of November, 2001

Attest:

NICHOLAS P. GODICI
Attesting Officer
Acting Director of the United States Patent and Trademark Office